United States Patent [19]
Drent et al.

[11] Patent Number: 6,156,936
[45] Date of Patent: Dec. 5, 2000

[54] HYDROFORMYLATION OF OLEFIN FEEDS CONTAINING DIENES

[75] Inventors: Eit Drent; Frederik Hendrik Van Der Steen; Robert Moene, all of Amsterdam, Netherlands

[73] Assignee: Shell Oil Company, Houston, Tex.

[21] Appl. No.: 09/256,600

[22] Filed: Feb. 23, 1999

[30]  Foreign Application Priority Data

Mar. 16, 1998  [EP]  European Pat. Off. ............. 98200827

[51] Int. Cl.⁷ .................................................. C07C 45/50
[52] U.S. Cl. ........................................... 568/454; 568/451
[58] Field of Search ..................... 568/451, 454

[56]  References Cited

U.S. PATENT DOCUMENTS

| | | | |
|---|---|---|---|
| 5,288,918 | 2/1994 | Maher et al. | 568/454 |
| 5,675,041 | 10/1997 | Kiss et al. | 568/454 |

FOREIGN PATENT DOCUMENTS

| | | |
|---|---|---|
| 0495547 | 1/1992 | European Pat. Off. . |
| 0900776 A1 | 3/1999 | European Pat. Off. ........ C07C 45/50 |
| 1127965 | 12/1966 | United Kingdom . |
| 2306344 | 5/1997 | United Kingdom ............ C07C 26/16 |
| 95/05354 | 2/1995 | WIPO . |

OTHER PUBLICATIONS

European Search Report dated Nov. 16, 1999.

*Primary Examiner*—Sreeni Padmanabhan

[57]  ABSTRACT

A process for the hydroformylation of a feed comprising compounds having a single ethylenically unsaturated group by reaction thereof in the liquid phase with carbon monoxide and hydrogen in the presence of a catalyst system comprising
a) a source of palladium cations;
b) a source of anions;
c) a source of at least one bidentate ligands of the formula $$R^1R^2M^1RM^2R^3R^4 \qquad (I)$$

characterized in that the ethylenically unsaturated feed comprises one or more dienes and/or further multiply unsaturated alkenes to an amount of 0.005–5 wt % based on the total amount of ethylenically unsaturated compounds in the feed, and in that component b) of the catalyst system is a source of anions of an acid having a pKa value, measured in aqueous solution at 18° C., of between −1 and 4.

7 Claims, No Drawings

HYDROFORMYLATION OF OLEFIN FEEDS CONTAINING DIENES

FIELD OF THE INVENTION

The invention relates to a process for the hydroformylation of ethylenically unsaturated compounds by reaction thereof with carbon monoxide and hydrogen in the presence of a catalyst.

BACKGROUND OF THE INVENTION

The hydroformylation of ethylenically unsaturated compounds to form aldehydes and/or alcohols is of considerable industrial importance. The process has been in commercial operation for decades and over the years much development work has been done to optimise the reaction conditions, the catalyst system and the equipment. Although significant progress towards higher yield and product selectivity has been made, further improvement of the process is still needed.

In the present applicant's WO 95/05354 there is disclosed a hydroformylation process whereby the catalyst system comprises a source of platinum group metal cations, preferably palladium or platinum cations, a source of anions other than halide anions, a source of bidentate ligands as defined below and a catalyst promoter comprising a source of halide anions. It is shown that the presence of the halide anion accounts for a considerably enhanced activity and selectivity of the process, i.e. suppression of paraffin make. However, the catalyst composition appeared to be sensitive to small variations of halide ion concentrations, the positive effect of which having a sharp peak at a molar ratio to the cation of about 0.4:1. In the subsequent present applicant's U.S. patent application Ser. No. 08/918.981, filed on Aug. 27, 1997, it is disclosed that the addition of water, in an amount of more than 0.6 wt % based on the total of the reaction mixture and up to its solubility limits under the reaction conditions, acts as a strong co-promoter with the halide anions.

In the aforementioned previous work, it was indicated with regard to the source of anions in the catalyst composition that any compound generating these anions may be used, preferably strong acids having a pKa value of less than 3 when measured in aqueous solutions at 18° C. and most preferably derivatives of sulphonic acid such as methane sulphonic acid (pKa=−1.9), trifluoromethane-sulphonic acid (pKa=−5,7) and tert.butanesulphonic acid (pKa=−1.2).

The present inventors unexpectedly found that the catalyst compositions as described above generally suffer from the disadvantage that they are rather sensitive to even small amounts, from 0.005 wt % based on the total amount of the ethylenically unsaturated compounds in the feed upward, of diene and/or further multi-unsaturated alkenes in the reaction feed. The latter, in particular dienes, were found to form relatively stable complexes with the metal (cation) of the catalyst, thus hindering the progress of the reaction. In other words, dienes were found to be strong albeit reversible catalyst inhibitors. When the hydroformylation reaction is performed in batch operation, the presence of dienes and/or further multi-unsaturated alkenes in the feed results in a significant slowing of the reaction. When the hydroformylation reaction is performed in continuous operation, their presence in the feed may result in impractically low production rates.

It has now been found that by a careful selection of the anions in the catalyst compositions based on palladium, as they are more broadly defined in WO 95/05354, the hydroformylation reaction can proceed efficiently even when up to 10 wt % of the olefinically unsaturated compounds in the feed are dienes and/or further multiply unsaturated alkenes. According to the present invention the anions have a pKa of between −1 and 4.

SUMMARY OF THE INVENTION

The present invention defines a process for the hydroformylation of a feed comprising compounds having a single ethylenically unsaturated group by reaction thereof in the liquid phase with carbon monoxide and hydrogen in the presence of a catalyst system comprising
a) a source of palladium cations;
b) a source of anions;
c) a source of at least one bidentate ligand of the formula $$R^1R^2M^1RM^2R^3R^4 \qquad (I)$$

wherein $M^1$ and $M^2$ independently represent a phosphorus, arsenic or antimony atom, R represents a bivalent bridging group containing from 1–4 atoms in the bridge, $R^1$ and $R^2$ independently represent a substituted or unsubstituted hydrocarbyl group, or together represent a bivalent substituted or unsubstituted cyclic group whereby the two free valencies are linked to $M^1$, and $R^3$ and $R^4$ independently represent a substituted or unsubstituted hydrocarbyl group, or together represent a bivalent substituted or unsubstituted cyclic group whereby the two free valencies are linked to $M^2$; and
d) a source of halide chosen from the group of chloride, iodide and bromide and mixtures thereof; characterized in that the ethylenically unsaturated feed comprises one or more dienes and/or further multiply unsaturated alkenes in an amount of from 0.005 to 10 wt % based on the total amount of ethylenically unsaturated compounds in the feed, and in that component b) of the catalyst system is a source of anions of an acid having a pKa value, measured in aqueous solution at 18° C., of between −1 and 4.

DETAILED DESCRIPTION OF THE INVENTION

Examples of suitable palladium sources are palladium compounds such as salts of palladium, e.g. carboxylates with up to 12 carbon atoms, palladium complexes, e.g. with carbon monoxide or acetylacetonate, or palladium combined with a solid material such as an ion exchanger or carbon. Palladium(II) acetate and palladium(II) acetylacetonate are examples of preferred palladium sources. Palladium compounds can be formed in situ by the reaction of 0-valent Pd compounds, such as palladium dibenzylidene acetone and tetrakis triphenyl phosphine palladium, with acids.

In bidentate ligands of formula I, i.e. component c) of the catalytic system, it is preferred that at least $R^1$ and $R^2$, more preferably also $R^3$ and $R^4$, together represent a bivalent substituted or unsubstituted cyclic group.

In bidentate ligands of formula (I), $M^1$ and $M^2$ are preferably the same. More preferably they are both phosphorus atoms, in which case the ligands are bisphosphines.

In the bridging group, represented by R, typically all bridging groups are carbon atoms, however, one or more of Si, N and P may also be present in the bridge.

Preferably the bridging group contains two or three, more preferably two, carbon atoms in the bridge.

The bivalent (substituted) cyclic group, represented by $R^1$ together with $R^2$, in general comprises at least ring atoms and preferably contains from 6 to 9 ring atoms. More preferably the cyclic group contains 8 ring atoms. Substituents, if any, are usually alkyl groups having from 1 to 4 carbon atoms. As a rule, all ring atoms are carbon atoms, but bivalent cyclic groups containing one or two heteroatoms in the ring, such as oxygen- or nitrogen, atoms are not precluded. Examples of suitable bivalent cyclic groups are 1,4-cyclohexylene, 1,4-cycloheptylene, 1,3-cycloheptylene, 1,3-cyclooctylene, 1,4-cyclooctylene, 1,5-cyclooctylene, 2-methyl-1,5-cyclooctylene, 2,6-dimethyl-1,4-cyclooctylene and 2,6-dimethyl-1,5-cyclooctylene groups.

Preferred bivalent cyclic groups are selected from 1,4-cyclooctylene, 1,5-cyclooctylene, and methyl (di)substituted derivatives thereof.

Mixtures of ligands comprising different bivalent cyclic groups may be used as well, e.g. mixtures of ligands with 1,4-cyclooctylene and ligands with 1,5-cyclooctylene groups.

In the ligands of formula (I), $R^1$, $R^2$, $R^3$ and $R^4$ independently may optionally be substituted with substituents such as alkoxy groups with 1 to 4 carbon atoms, halogen atoms or ($C_1$ to $C_4$ alkyl)amino groups.

Examples of such substituents are alkyl groups such as ethyl, isopropyl, sec-butyl and tert-butyl groups, cycloalkyl groups such as cyclopentyl and cyclohexyl groups, aryl groups such as phenyl and tolyl groups and bivalent groups such as a hexamethylene group.

However, preferably $R^3$, together with $R^4$ represents a bivalent cyclic group, in particular the same group as the group represented by $R^1$ together with $R^2$, in which case the two free valencies of each bivalent cyclic group are, of course, linked to $M^2$ and $M^1$, respectively.

Preferred bidentate ligands of formula (I) are 1,2-bis(1,4-cyclooctylenephosphino)ethane, 1,2-bis(1,5-cyclooctylenephosphino)ethane and mixtures thereof.

For the preparation of the bidentate ligands, reference is made to known techniques, for example the method disclosed in GB-A-1,127,965.

Preferably, the molar ratio between the halide anions d) and the palladium a) is between 0.02:1 and 3:1. More preferably, the molar ratio between halide anions and palladium cations is at most 2:1, even more preferably less than 1:1, for instance from 0.02:1 to 1:1.

As a source of halide anions any compound generating halide anions under the reaction conditions may be used.

Recommended are inorganic compounds such as hydrogen halides, e.g. HCl, HBr and HI and metal halides, e.g. NaCl, $MgBr_2$, $ZnCl_2$, $ZnI_2$, KBr, RbCl, CsCl, CsI, $MgI_2$ and CuCl.

Another category of recommended sources of halide anions consists of halogen containing organic compounds which are capable of providing halide anions to the reaction medium. Suitable are for example organic phosphonium halides, such as triarylalkyl phosphonium chloride and halogen containing aromatic compounds such as 5-halobenzoic acids, e.g. 5-chlorobenzoic acid, 2,5-dichlorobenzoic acid, 2,3,5-tri-iodobenzoic acid, 3,5-di-iodobenzoic acid, m-halophthalic acids and esters thereof.

Catalyst promoters comprising a source of chloride anions are in particular preferred.

Preferably water is also present, in an amount of more than 0.6 wt % based on the total amount of the reaction mixture and up to its solubility limit under the reaction conditions. More preferably the amount of water is between 0.7 and 3.0 wt %, based on the total of the reaction mixture.

The source of anions according to the invention has a pKa value, when measured in aqueous solution at 18° C., of between −1 and 4. Preferably the source of anions is an acid according to the formula $$RXO_3H_2 \qquad (II)$$

wherein X represents phosphorus, arsenic or antimony and R represents a substituted or unsubstituted alkyl or aryl group, or OH. The preferred X is phosphorus. A preferred source of anions can also be a salt of an acid according to formula (II). The salts can e.g. be metal salts, ammonium salts and phosphonium salts.

Examples of sources of anions according to the invention are phosphoric acid, phosphates, phosphonates, benzenephosphonic acid, tert. butanephosphonic acid and the corresponding arsenic and antimony compounds.

The quantity in which the catalyst system is used, is not critical and may vary within wide limits. Usually amounts in the range of $10^{-8}$ to $10^{-1}$, preferably in the range of $10^{-7}$ to $10^{-2}$ mole atom of palladium per mole of ethylenically unsaturated compound are used. The amounts of the participants in the catalyst system are conveniently selected such that per mole atom of palladium from 0.5 to 10, preferably from 1 to 6 moles of bidentate ligand are used, and from 0.5 to 15, preferably from 1 to 8 moles of the anion source.

The ethylenically unsaturated feed is preferably one having from 2 to 30, more preferably from 4 to 24 carbon atoms per molecule, or a mixture thereof. In the process of the present invention the feed comprises from 0.005 to 10 wt % of dienes and/or further multiply unsaturated alkenes such as trienes and tetraenes, based on the total amount of ethylenically unsaturated compounds in the feed.

Although the catalyst system according to the invention will also work with any amount of dienes and/or further multilpy unsaturated alkenes below 0.005 wt %, the advantages of the invention are only apparent within the given range. More in particular, the range is from 0.05 to 5 wt %, even more in particular from 0.05 to 1 wt %.

The dienes and/or further multiply unsaturated alkenes present in the feed according to the invention may be conjugated and/or non-conjugated, and they preferably contain between 4 and 30 carbon atoms.

Preferably the main part of the feed comprises an internal mono-olefin having from 4 to 24 carbon atoms, or mixtures thereof. Such olefin mixtures are commercially readily available, for example the olefin mixtures, obtained as products of a process for the oligomerisation of ethylene, followed by a double bond isomerisation and disproportionation reaction. In the process of the invention, these internal olefins, usually mixtures of linear internal olefins with 6 to 20 carbon atoms per molecule, or closer boiling fractions of such mixtures, can be hydroformylated at high rates and complete conversion. Examples are mixtures of linear internal $C_6$ to $C_8$ olefins, and of linear internal $C_{10}$ to $C_{14}$ olefins.

Substituted olefins may also be used, for example unsaturated carboxylic acids, esters of such acids, e.g. methyl pentenoate, or unsaturated esters of carboxylic acids, e.g. allylacetate.

If desired, branched olefins may be used, but the hydroformylation product will then of course contain branched structures as well.

Hydrogen and carbon monoxide may be supplied in equimolar or non-equimolar ratios, e.g. in a ratio within the range of 8:1 to 1:4, typically 4:1 to 1:2. Preferably they are supplied in a ratio within the range of 3:1 to 1:2.

The hydroformylation can be suitably carried out at moderate reaction conditions. Hence temperatures in the range of 50 to 200° C. are recommended, preferred temperatures being in the range of 70 to 160° C. Reaction pressures in the range of 500 to 10000 kPa are preferred. Lower or higher pressures may be selected, but are not considered particularly advantageous. Moreover, higher pressures require special equipment provisions.

In the process of the invention, the ethylenically unsaturated starting material and the formed hydroformylation product may act as reaction diluent. Hence, the use of a separate solvent is not necessary. Conveniently, however, the hydroformylation reaction may be carried out in the additional presence of a solvent. As such, saturated hydrocarbons, e.g. paraffins and isoalkanes are recommended and furthermore alcohols, preferably having from 4 to 10 carbon atoms per molecule, such as butanol, ethylhexanol-1, nonanol-1, or in general terms the alcohols formed as hydroformylation product, ethers such as 2,5,8-trioxanonane (diglyme), diethylether and anisole, and ketones, such as methylbutylketone.

In earlier hydroformylation processes, such as the process according to EP-A-0,495,547, the use of an alcohol as a solvent was often considered undesirable, since the used hydroformylation catalysts were also catalytically active in the formation of esters in a reaction involving an olefin, carbon monoxide and the solvent alcohol. However, the catalyst systems of the present invention in view of their high selectivity towards the desired hydroformylation product, allow the use of alcohols as solvent.

Solvents containing strong polar groups are in particular preferred if the unsaturated starting material has a relatively low molecular weight, i.e., if ethylenically unsaturated compounds having from 5 to 7 carbon atoms are used.

For the hydroformylation of higher molecular weight unsaturated compounds, e.g. olefins having from 10 to 18 carbon atoms the use of less polar inert solvents will usually be satisfactory.

Solvents, comprising or substantially consisting of sulphones are preferred. Sulphones are in particular preferred, for example dialkylsulphones such as dimethylsulphone and diethylsulphone and cyclic sulphones, such as sulfolane (tetrahydrothiophene-1,1-dioxide), 2-methylsulfolane and 2-methyl-4-ethyl-sulfolane.

Sulfolane has proved to be a most effective solvent.

Mixtures of solvents may also be used, for example a mixture of a sulphone with a protic solvent, such as an alcohol.

The amount of solvent to be used in the process of the invention may vary considerably. It is within the reach of those skilled in the art to establish in each case the optimal amount of solvent required.

The invention will be illustrated by the following examples.

EXAMPLES

The experiments were carried out in a 300 ml magnetically stirred Hasteloy autoclave.

The autoclave was charged with the feed material, this being 30 ml of a mixture of $C_{11}/C_{12}$ alpha olefins which did or did not contain 0.25 or 5.0 ml of 1,7 octadiene (Examples 1–9); or 50 ml of a gasoline having a boiling point range of 85–145° C., a total $C_6$–$C_9$ olefins content of 27.6 wt %, a total dienes content of 1 wt % and a sulphur content of 0.09 wt % (Examples 10 and 11).

The autoclave was further charged with 30 ml ethylhexanol, 0.5 ml water and 10 ml sulfolane wherein there were dissolved 0.25 mmol palladium (II) acetate, 0.4 mmol of the ligand 1,2-bis(1,4-cyclooctylene-phosphino) ethane (BCPE), 0.5 mmol of the anion and 0.1–0.3 mmol of the halide.

After having been flushed, the autoclave was pressurised with carbon monoxide and hydrogen to a partial pressure of 2000 and 4000 kPa respectively. Subsequently the reactor was sealed and the contents were heated to the pre-set temperature and maintained at that temperature until 80 wt % of the feed material was converted (as determined by the pressure decrease in the autoclave).

After cooling, a sample of the contents of the reactor was taken and analysed by Gas Liquid Chromatography—to determine the (undesired)paraffin make as wt % of the mainly alcoholic product.

Further details are presented in Table I.

TABLE I

| Ex. | Olefin feed (ml) | Diene added (ml) | Catalyst anion source (mmol) | Halide promoter (mmol) | Reaction Temp. (° C.) | Time to 80% Conversion (hrs) | Main Products | Paraffin make (wt % of total product) |
|---|---|---|---|---|---|---|---|---|
| 1* | $C_{11}/C_{12}$ (30) | none | $CF_3SO_3H$ (0.5) | HCl (0.1) | 105 | 1 | $C_{12}/C_{13}$ alcohols | 1.0 |
| 2* | $C_{11}/C_{12}$ (30) | 1,7 octadiene (0.25) | $CF_3SO_3H$ (0.5) | HCl (0.1) | 105 | >15 | | |
| 3* | $C_{11}/C_{12}$ (30) | 1,7 octadiene (0.25) | $CF_3SO_3H$ (0.5) | HCl (0.1) | 145 | 10 | $C_{12}/C_{13}$ alcohols | 6 |
| 4* | $C_{11}/C_{12}$ (30) | 1,7 octadiene (0.25) | $CF_3SO_3H$ (0.5) | HCl (0.3) | 145 | 4 | $C_{12}/C_{13}$ alcohols | 4.2 |
| 5* | $C_{11}/C_{12}$ (30) | 1,7 octadiene (0.25) | t-Butane $SO_3H$ (0.5) | HCl (0.3) | 145 | 4.5 | $C_{12}/C_{13}$ alcohols | 1.8 |
| 6 | | 1,7 octadiene (0.25) | $H_3PO_4$ (0.5) | HCl (0.2) | 145 | 2 | $C_{12}/C_{13}$ alcohols | 1.2 |
| 7 | $C_{11}/C_{12}$ (30) | 1,7 octadiene (0.25) | $H_3PO_4$ (0.5) | HCl (0.3) | 145 | 2 | $C_{12}/C_{13}$ alcohols | 1.2 |
| 8 | $C_{11}/C_{12}$ (30) | 1,7 octadiene (0.25) | Phenyl-phosphonic acid (0.5) | HCl (0.2) | 145 | 1.5 | $C_{12}/C_{13}$ alcohols | 1.2 |
| 9 | $C_{11}/C_{12}$ (30) | 1,7 octadiene (5.0) | $H_3PO_4$ (0.5) | HCl (0.2) | 145 | 7 | $C_{12}/C_{13}$ alcohols | n.d. |

TABLE I-continued

| Ex. | Olefin feed (ml) | Diene added (ml) | Catalyst anion source (mmol) | Halide promoter (mmol) | Reaction Temp. (° C.) | Time to 80% Conversion (hrs) | Main Products | Paraffin make (wt % of total product) |
|---|---|---|---|---|---|---|---|---|
| 10 | gasoline (50) | | $H_3PO_4$ (0.5) | HCl (0.2) | 160 | 3.5 | $C_7$–$C_{10}$ alcohols | n.d. |
| 11* | gasoline (50) | | $CF_3SO_3H$ (0.5) | HCl (0.2) | 160 | >15 | | |

*Comparative example
n.d. = Not determined

We claim:

1. A process for the hydroformylation of a feed comprising compounds having a single ethylenically unsaturated group by reaction thereof in the liquid phase with carbon monoxide and hydrogen; in the presence of a catalyst system comprising:

a) a source of palladium cations;
b) a source of anions;
c) a source of at least one bidentate ligands of the formula

   (I)

wherein $M^1$ and $M^2$ independently represent a phosphorus, arsenic or antimony atom, R represents a bivalent bridging group containing from 1–4 carbon atoms, optionally also one or more of Si, N, or P, in the bridge, $R^1$ and $R^2$ independently represent a substituted or unsubstituted hydrocarbyl group, or together represent a bivalent substituted or unsubstituted cyclic group whereby the two free valencies are linked to $M^1$, and $R^3$ and $R^4$ independently represent a substituted or unsubstituted hydrocarbyl group, or together represent a bivalent substituted or unsubstituted cyclic group whereby the two free valencies are linked $M^1$, and $R^3$ and $R^4$ independently represent a substituted or unsubstituted hydrocarbyl group, or together represent a bivalent substituted or unsubstituted cyclic group whereby the two free valencies are linked to $M^2$; and d) a source of halide chosen from the group of chloride, iodide and bromide and mixtures thereof; characterized in that the ethylenically unsaturated feed comprises one or more dienes and/or further multiply ethylenically unsaturated alkenes to a total amount of 0.005–10 wt % based on the total amount of ethylenically unsaturated compounds in the feed, and in that component b) of the catalyst system is a source of anions of an acid having a pKa value, measured in aqueous solution at 18° C., of between −1 and 4 and wherein said source of anions b) is an acid according to the formula: $RXO_3H_2$ (II), wherein X represents phosphorus, arsenic or antimony and R represents a substituted or unsubstituted alkyl or aryl group, or OH, or a salt thereof.

2. A process according to claim 1, characterized in that in the bidentate ligand of formula (I) $R^1$ and $R^2$ together represent a bivalent substituted or unsubstituted cyclic group whereby the two valencies are linked to $M^1$.

3. A process according to claim 1, characterized in that in the bidentate ligand of formula (I) both of $M^1$ and $M^2$ are phosphorus and R is $CH_2$—$CH_2$ or $CH_2$—$CH_2$—$CH_2$.

4. A process according to claim 2, characterized in that in the bidentate ligand of formula (I) each of the bivalent cyclic groups, represented by $R^3$ together with $R^4$ and/or $R^1$ together with $R^2$ respectively, is a cycloalkylene group having from 6 to 9 ring atoms.

5. A process according to claim 1, characterized in that X is phosphorus.

6. A process according to claim 1, characterized in that the source of anions b) is chosen from the group of phosphoric acid, phosphates, phosphonates, benzenephosphonic acid, tert. butanephosphonic acid and the corresponding arsenic and antimony compounds.

7. A process according to claim 1, characterized in that the halide d) is chloride.

* * * * *